United States Patent [19]

Shiono et al.

[11] Patent Number: 5,352,216
[45] Date of Patent: Oct. 4, 1994

[54] STRETCH FABRIC FOR MEDICAL USE

[75] Inventors: Katuaki Shiono, Hatogaya; Koji Usukura, Kasukabe, both of Japan

[73] Assignee: Alcare Co., Ltd., Tokyo, Japan

[21] Appl. No.: 978,194

[22] Filed: Nov. 18, 1992

Related U.S. Application Data

[63] Continuation of Ser. No. 602,760, Oct. 24, 1990, abandoned.

[30] Foreign Application Priority Data

Oct. 26, 1989 [JP] Japan ................. 1-279500

[51] Int. Cl.⁵ ............... A61F 7/00; A61F 13/15; A61F 13/20; A61L 15/00
[52] U.S. Cl. ................. 604/312; 604/365; 604/369; 604/378; 604/380; 602/60; 602/75; 602/76; 602/77
[58] Field of Search .............. 2/243 A; 428/137, 284, 428/287; 604/312, 358, 366–367, 369, 372, 378, 370, 380; 602/43–45, 47, 76, 77, 60, 75

[56] References Cited

U.S. PATENT DOCUMENTS

| | | | |
|---|---|---|---|
| 2,788,003 | 4/1957 | Morin | 604/380 |
| 3,526,224 | 9/1970 | Potts | 602/43 |
| 3,842,832 | 10/1974 | Wideman et al. | 602/75 |
| 3,955,575 | 5/1976 | Okuda | 604/377 |
| 4,244,367 | 1/1981 | Rollenhagen | 604/396 |
| 4,537,822 | 8/1985 | Nanri et al. | 428/284 |
| 4,551,144 | 11/1985 | Graber | 604/378 |
| 4,961,418 | 10/1990 | McLaurin-Smith | 128/157 |
| 4,984,570 | 1/1991 | Langen et al. | 604/304 |
| 5,017,424 | 5/1991 | Farnworth et al. | 2/1 |
| 5,061,258 | 10/1991 | Martz | 128/898 |
| 5,114,418 | 5/1992 | Levy | 604/372 |
| 5,229,191 | 7/1993 | Austin | 604/378 |

FOREIGN PATENT DOCUMENTS 2081177 2/1982 United Kingdom ............. 602/75

Primary Examiner—Randall L. Green
Assistant Examiner—P. Zuttarelli
Attorney, Agent, or Firm—Haverstock, Garrett & Roberts

[57] ABSTRACT

A composite stretch fabric is disclosed that is comprised of a laminate of three layers, the center layer being comprised of a web of a nonwoven polyurethane resin with a basis weight in the range of 50–250 g/m² and an air permeability of at least 10 cc/sec/cm² with stretchable fabric layers adhered to each side thereof, one of which can be a nylon pile and the other of which is a double knit fabric that can be of porous, hollow fiber for sweat absorption, the composite can also be embossed.

5 Claims, 1 Drawing Sheet

STRETCH FABRIC FOR MEDICAL USE

This is a continuation of copending application(s) Ser. No. 07/602,760 filed on Oct. 24, 1990, abandoned.

DETAILED DESCRIPTION OF THE INVENTION

The present invention relates to the material used for supporters and medical appliances for the purpose of warmth retention, protection, support and fixation, and more specifically, a stretch fabric for medical use which provides high air permeability and is not bulky, but elastic in all directions, and well-fitting.

The supporters and medical appliances for the purpose of warmth retention, protection, support, and fixation include supporters to retain heat and protect joints of shoulders, elbows, wrists, knees, and ankles and muscles of upper arms, forearms, thighs, and shins at the time of exercising and sports participation and supporters and appliances used in pathological diseases of the aforementioned physical portions. The supporters used in the present invention mean those with a cylindrical limb-fitting structure, while the appliances mean those with structure that can cover the affected portions and can be joined by velcro fasteners, hooks, or chuck fasteners when they are worn.

For the material of these supporters and appliances knitted fabrics, such as knitted fabrics with covered stretch fiber yarns, woven fabrics, or fabrics to which elastomeric sheets or foams are applied or adhered onto or stretch fabrics which are adhered to both sides of elastomeric foams (formed of natural rubber, neoprene rubber, urethane, plasticized vinyl chloride, EVA, and polybutadiene rubber systems, etc.) are well known. These materials are formed either cylindrically or the material finished in a flat sheet is used independently or combined, or assembled with other materials to build up a structure that fits the profile of the diseased portions. However, there is no stretch fabric which satisfies all the requirements for air permeability, aesthetic appearance, weight, multidirectional stretchability, and shape preservation. All of them have defects, including that they become stuffy when they are worn, are hardly able to be worn as underwear due to the heavy weight, generate curls or are dislocated when they are worn; none of them can be worn comfortably for a long time.

That is, knitted fabric, for example, fabric of covered yarn stretch fiber, has excellent air permeability but has only one stretch direction, and the material itself lacks firmness, causing curling or dislocation when it is worn. To overcome these defects, an elastomer processed into film or a foam consisting of elastomer is laminated to such fabric.

This has improved stretchability in multidirections and firmness of the material itself, but on the other hand, it has significantly degraded air permeability, producing the defect of stuffiness in use. The fabric whose one side consists of elastomer processed into film or laminated with a foam displays different stretchability between the two surfaces, producing greater curling and deformation. Then, a fabric using an elastomeric foam as a core was developed, to both surfaces of which knitted fabric is laminated. This has greatly improved deformation, which used to be a defect of the fabric, when only one surface of which is processed with elastomer, and this has greatly increased firmness and stability in use, but it hardly provides air permeability, whether the foam consists of closed cells or open cells. This causes excessive stuffiness and bulkiness and results in poor wearing comfort and heavy weight. This is a problem, particularly for sport use and in elderly people and children.

PROBLEMS THAT THE INVENTION SOLVES

The objective of the present invention is to solve the defects of conventional stretch fabrics and to provide a stretch fabric for medical use which provides good air permeability, light weight, multidirectional stretchability, and shape preservation, is free from stuffiness and curling, and perfectly fits the portion to which applied when it is used as a material for supporters and appliances, and worn for an extended time.

MEANS OF SOLVING PROBLEMS

In order to solve the above-mentioned problems, the stretch fabric for medical use of the present invention has the stretch fabric layer which is laminated onto both surfaces of a nonwoven fabric layer prepared by directly spinning an elastomeric resin. This has a three-layer construction, that is, a stretch fabric layer, a nonwoven fabric layer prepared by directly spinning elastomeric resin, and a second stretch fabric layer.

For the nonwoven fabric layer prepared by directly spinning an elastomeric resin, that consisting of polyurethane resin is suitable, and the nonwoven fabric which is prepared by melting polyurethane resin, extruding from a nozzle in yarn form and drawing and random piling to produce preferably a spun bonded web having a weight per unit area of 50 to 250 $g/m^2$ is advantageous.

As the stretch fabric layer, knitted cloth using cotton, rayon, polyacrylonitrile, polyamide, or polyester yarns, or knitted or woven fabric with stretchability produced by incorporating a stretch yarn such as polyurethane into the above-mentioned knitted cloth are desirable. For the stretch fabric layer placed on the outside, nylon which is pile-knitted and fastened with velcro fasteners can be used, while for the stretch fabric layer making contact with the skin, a knitted fabric with sweat absorbing diffusing capability, for example, a double knit fabric with a water absorbing layer, such as "CONTROL" of ASAHI CHEMICAL INDUSTRY CO., LTD., or "FIELD SENSOR" of TORAY INDUSTRIES, INC., or a fabric knitted from porous hollow fibers such as "WELKEY" of TEIJIN LIMITED is used to absorb, transfer, and diffuse sweat from the skin to the outside, which is particularly advantageous.

In the laminating of both stretch fabric layers and nonwoven fabric layer, bonding by adhesives is desirable. The elastomer-based adhesives include natural rubber, neoprene, polyacrylonitrile, polyurethane, styrene-butadiene solvent or emulsion type adhesives, and styrene-isoprene-styrene, styrene-butadiene-styrene, styrene-ethylene, and butadiene-styrene thermoplastic adhesives.

As a specific lamination method, one method is to apply adhesives to one surface of the nonwoven fabric layer and the rear surface of one stretch fabric layer, then bring the layers together and place under pressure while allowing them to pass a heater, and take up into a roll after cooling. Then, adhesive is applied to the other surface of the nonwoven fabric layer while unwinding the roll, and the surface is bonded together with the other stretch fabric surface, the rear surface of which is supplied with adhesive, and put under pressure while it is again allowed to pass the heater.

Another method is to apply adhesive on one surface of the nonwoven fabric and one rear surface of the stretch fabric, bring together after half-drying and place under pressure, then to apply adhesive to the other surface of the nonwoven fabric layer and the rear surface of the other stretch fabric layer, bring together under semi-drying condition and place under pressure.

Still another method is to process in advance hot-melt elastomeric adhesives onto two surfaces of the nonwoven fabric layer and each inside surface of the two stretch fabric layers, stack the three layers together, and heat and pressurize to bond and laminate.

Referring now to the drawings, embodiments according to the present invention will be described in detail hereinafter.

Figure 1:
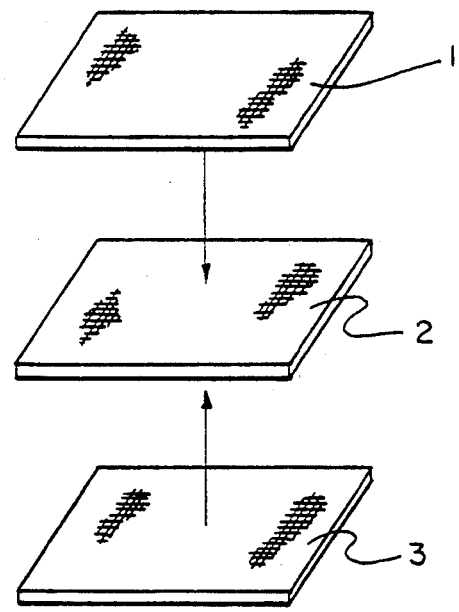
FIG. 1 shows components of the stretch fabric for medical use according to the present invention in a dissociated form. Numeral 1 is the first stretch fabric layer, 2 the nonwoven fabric layer prepared by directly spinning elastomeric resin, and 3 the second stretch fabric layer. By bonding the first stretch fabric layer 1 and nonwoven fabric layer 2, the second stretch fabric layer 3 and nonwoven fabric layer 2, respectively, with adhesives, the stretch fabric of the three-layer structure as shown in FIG. 2 is obtained.
Figure 2:
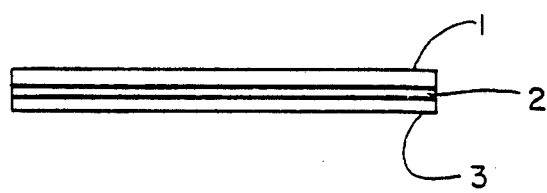

Three specific embodiments are described hereunder and one comparative example is described to compare properties.

EMBODIMENT 1

The commercial spun bonded nonwoven fabric named "ESPANSIONE", which is commercially available from Kanebo Ltd. and whose weight per area is 190 g/m$^2$, 50% modulus of 0.7 kg/cm lengthwise and 0.9 kg/cm crosswise and air permeability of 20 cc/sec/cm$^2$, is used for the nonwoven fabric layer and is prepared by directly spinning polyurethane resin. A stretchable French pile of napped mixed nylon and polyurethane fibers whose 50% modulus is 0.6 kg/cm lengthwise, 0.6 kg/cm crosswise and air permeability is more than 50 cc/sec/cm$^2$ is used for the outer stretch fabric. For the inner surface stretch fabric layer which makes contact with the skin, a sweat absorbing diffusing type knitted fabric consisting of polyester fiber capillaries (Toray's "Field Sensor") whose 50% modulus is 0.7 kg/cm lengthwise and 0.5 kg/cm crosswise, and air permeability is more than 50 cc/sec/cm$^2$ is used.

On one side of the above-mentioned nonwoven fabric layer, an acrylate system adhesive is applied at 35 g/m$^2$ with a roll coater, and on the rear side of the stretchable French pile, which constitutes the outside stretch fabric layer, the acrylate adhesive is applied at 30 g/m$^2$ with a roll coater. The two surfaces are bonded together and pressurized between pressure rolls while they are allowed to pass a 70°–80° C. heater and taken up in a roll form after cooling. Then, on the other surface of the nonwoven fabric layer, acrylate adhesive is applied at 35 g/m$^2$ with a roll coater while the roll is being unwound, then to the sweat absorbing diffusing type knitted fabric consisting of the stretch fabric layer making contact with the skin, the same acrylate adhesive is applied at 25 g/m$^2$, and these two adhesive-supplied surfaces are bonded together, and passed through pressure rolls several times while they are allowed to pass a 70°–80° C. heater, then taken up to make the stretch fabric for medical use.

EMBODIMENT 2

As a nonwoven fabric layer a nonwoven fabric produced by the melt-blown process, a kind of direct spinning process for polyurethane resin, the product of Tomen Chemical Corp. whose weight per area is 100 g/m$^2$, 50% modulus of 0.5 kg/cm lengthwise and 0.6 kg/cm crosswise, and air permeability of 20 cc/sec/cm$^2$, is used. For the outer surface stretch fabric layer, nylon tricot whose 50% modulus is 0.3 kg/cm lengthwise, 0.25 kg/cm crosswise, and air permeability of more than 50 cc/sec/cm$^2$ is used, and for the other surface stretch fabric layer which makes contact with the skin, a cotton pile fabric whose 50% modulus is 0.8 kg/cm lengthwise and 1.2 kg/cm crosswise and air permeability of more than 40 cc/sec/cm$^2$ is used.

On one side of the above-mentioned nonwoven fabric layer, a polyurethane-based adhesive is sprinkled at 30 g/m$^2$, and on the rear side of the nylon tricot stretch fabric layer the same adhesive is sprinkled at 25 g/m$^2$. The two surfaces are bonded together and are treated in the same manner as in Embodiment 1 and taken up in a roll form. Then, on the remaining surface of the nonwoven fabric layer and the rear surface of the other stretch fabric layer, polyurethane-based adhesive is sprinkled in the same manner, and the surfaces are treated in the same manner as in Embodiment 1 and made into stretch fabric for medical use.

EMBODIMENT 3

The commercial nonwoven fabric named "ESPANSIONE", which is commercially available from Kanebo, Ltd., and whose weight per unit area is 150 g/m$^2$, 50% modulus of 0.6 kg/cm lengthwise and 0.8 kg/cm crosswise, and air permeability of 12 cc/sec/cm$^2$, is used for the nonwoven fabric layer prepared by directly spinning polyurethane resin, and the surface is embossed with a rhombus pattern with an embossing roll engraved with a rhombus pattern whose surface temperature is set to 180°–190° C. The rhombus pattern covered approximately 43% of the overall area. For the stretch fabric layer, a stretchable French pile is used for the outside and a sweat absorbing diffusing type knitted fabric consisting of polyester fiber used on the skin contacting side as in Embodiment 1.

On one side of the above-mentioned nonwoven fabric layer, a SIS (strene-isoprene-styrene copolymer) thermoplastic adhesive is applied at 45 g/m$^2$ in dots and immediately the stretchable French pile is bonded together with the nonwoven fabric, allowed to pass through pressure rolls, and taken up in a roll after cooling. Then on the other surface of the nonwoven fabric layer, SIS is applied at 45 g/m$^2$ in dots while the roll is being unwound, and immediately bonded to a moisture absorbing diffusing type knitted fabric consisting of polyester fibers, and the stretch fabric for medical use is prepared.

COMPARATIVE EXAMPLE

Neoprene rubber foam (expansion ratio: 30, thickness: 3 mm) is used in place of the polyurethane nonwoven fabric according to Embodiment 1, and as the stretch fabric layers on both sides of this neoprene rubber foam, a sweat absorbing diffusing type fabric consisting of the stretchable French pile and polyester fiber according to Embodiment 1 is used, and the three layers are bonded together with acrylate adhesive to make a stretch fabric for medical use.

The following table shows various properties of the embodiments and the comparative example.

TABLE 1

|  | Embodiment 1 | Embodiment 2 | Embodiment 3 | Comparative Example |
| --- | --- | --- | --- | --- |
| 50% Modulus (kg/cm) Lengthwise, Cross-wise | 1.8<br>1.4 | 1.2<br>0.9 | 1.7<br>1.6 | 1.3<br>1.2 |
| Air permeability (cc/sec/cm$^2$) | 5 | 7 | 4 | 0 |
| Weight (g/m$^2$) | 960 | 880 | 1,010 | 1,250 |

As is clear from the table, 50% modulus values are nearly similar to the comparative example, which is popularly used conventionally, securing sufficient fixing, supporting, and compressing forces. When air permeability is compared, the conventional fabric hardly provides any permeability, but the fabrics of the present invention provide high permeability. This indicates that the conventional fabric generates stuffiness in a short period, whereas that of the present invention does not generate stuffiness even if it is worn for a long time and assures excellent wearing comfort. This feature is, in particular, advantageous under high temperature high-humidity conditions. In addition, the weight of the present invention is reduced by more than 20% as compared to that of the comparative example.

EFFECTS OF THE INVENTION

The stretch fabric for medical use of the present invention has a construction wherein a stretch fabric layer is laminated onto both surfaces of a nonwoven fabric layer prepared by directly spinning an elastomeric resin, and solves most defects of the conventional high elastic sheet using neoprene rubber, urethane, butadiene rubber, or vinyl chloride foams as a core, which has a high specific gravity and large thickness, and hardly provides any air permeability. The stretch fabric for medical use of the present invention is extremely lightweight and free from stuffiness in use, and in addition, satisfies aesthetic requirements. The supporters and medical appliances formed with the stretch fabric of the present invention are well balanced from all the functional viewpoints, provide good wearing comfort, and, therefore, are extremely advantageous, in particular, for patients requiring long-time application, elderly people and children with diminished strength, and athletes practicing sports actively.

We claim:

1. A composite stretch fabric material for medical use comprising a nonwoven fabric layer having opposed first and second sides and being formed of a spun elastomeric resin arranged in a random web of fibers, said nonwoven fabric layer being formed of a polyurethane resin, said nonwoven layer being of a weight per unit area in a range of about 50–250 g/m$^2$ and having an air permeability rate per unit area of at least 10 cc/sec/cm$^2$, a first stretchable fabric layer laminated to the first side of said nonwoven fabric layer, and a second stretchable fabric layer laminated to the second side of said nonwoven fabric layer, said composite material formed by said first and second stretchable fabric layers and said nonwoven fabric layer, said composite material further being air permeable throughout all layers thereof and being elastic in all directions.

2. The composite stretch fabric material according to claim 1 wherein one of said first and second stretchable fabric layers includes a nylon pile fabric layer, and the other of said first and second stretchable fabric layers includes a sweat-absorbing evaporating stretch fabric.

3. The composite stretch fabric material according to claim 2 wherein the sweat-absorbing evaporating stretch fabric is a double knit fabric formed of a fabric knitted from porous hollow fibers.

4. The composite stretch fabric material according to claim 2 wherein the sweat-absorbing evaporating stretch fabric is double knit fabric.

5. The composite stretch fabric material according to claim 2 wherein said nonwoven fabric layer has a surface embossed with a rhombus pattern over at least a portion thereof.

* * * * *